US 12,344,579 B2
United States Patent
Zhang et al.

(10) Patent No.: US 12,344,579 B2
(45) Date of Patent: Jul. 1, 2025

(54) BUILT-IN MICRO-INTERFACE OXIDATION SYSTEM AND METHOD FOR PREPARING TEREPHTHALIC ACID FROM P-XYLENE

(71) Applicant: NANJING YANCHANG REACTION TECHNOLOGY RESEARCH INSTITUTE CO., LTD., Nanjing (CN)

(72) Inventors: Zhibing Zhang, Nanjing (CN); Zheng Zhou, Nanjing (CN); Feng Zhang, Nanjing (CN); Lei Li, Nanjing (CN); Weimin Meng, Nanjing (CN); Baorong Wang, Nanjing (CN); Gaodong Yang, Nanjing (CN); Huaxun Luo, Nanjing (CN); Guoqiang Yang, Nanjing (CN); Hongzhou Tian, Nanjing (CN); Yu Cao, Nanjing (CN)

(73) Assignee: NANJING YANCHANG REACTION TECHNOLOGY RESEARCH INSTITUTE CO., LTD., Nanjing (CN)

( * ) Notice: Subject to any disclaimer, the term of this patent is extended or adjusted under 35 U.S.C. 154(b) by 0 days.

(21) Appl. No.: 17/910,299

(22) PCT Filed: May 28, 2020

(86) PCT No.: PCT/CN2020/092767
§ 371 (c)(1),
(2) Date: Sep. 8, 2022

(87) PCT Pub. No.: WO2021/196386
PCT Pub. Date: Oct. 7, 2021

(65) Prior Publication Data
US 2023/0167043 A1 Jun. 1, 2023

(30) Foreign Application Priority Data
Mar. 31, 2020 (CN) .......................... 202010243427.X

(51) Int. Cl.
*C07C 51/265* (2006.01)
*B01D 3/14* (2006.01)
(Continued)

(52) U.S. Cl.
CPC .............. *C07C 51/265* (2013.01); *B01D 3/14* (2013.01); *B01D 5/0063* (2013.01); *B01J 4/001* (2013.01);
(Continued)

(58) Field of Classification Search
USPC ........................................................ 562/480
See application file for complete search history.

(56) References Cited

FOREIGN PATENT DOCUMENTS

| CN | 1431927 A | 7/2003 |
|---|---|---|
| CN | 105348067 A | 2/2016 |

OTHER PUBLICATIONS

Machine translation of CN105348067A, 11 pages, retrieved from ESPACENET on Aug. 16, 2023. (Year: 2016).*

(Continued)

*Primary Examiner* — Fred M Teskin
(74) *Attorney, Agent, or Firm* — Chun-Ming Shih; LANWAY IPR SERVICES

(57) ABSTRACT

The invention provides a built-in micro-interface oxidation system for preparing terephthalic acid from p-xylene. The oxidation system includes a first reactor, a rectifying tower and a second reactor which are sequentially connected. A first outlet is disposed on a side wall of the first reactor; a first inlet is disposed on a side wall of the second reactor; a material inlet is disposed on a side wall of the rectifying tower; and a material outlet is disposed at a bottom of the rectifying tower. The first outlet is connected with the material inlet of the rectifying tower; the first inlet is connected with the material outlet of the rectifying tower. Micro-interface units are arranged in the first reactor and the (Continued)

second reactor for dispersing and crushing air into bubbles. Through disposing micro-interface units in reactors, problems of high energy consumption, high raw material consumption and low reaction efficiency are solved.

7 Claims, 1 Drawing Sheet

(51) Int. Cl.
  *B01D 5/00* (2006.01)
  *B01J 4/00* (2006.01)
  *B01J 10/00* (2006.01)
  *B01J 19/24* (2006.01)
(52) U.S. Cl.
  CPC ........... *B01J 10/002* (2013.01); *B01J 19/245* (2013.01); *B01J 2204/002* (2013.01); *B01J 2204/005* (2013.01)

(56) References Cited

OTHER PUBLICATIONS

Machine translation of CN1431927A, 47 pages, retrieved from ESPACENET on Aug. 17, 2023. (Year: 2003).*

* cited by examiner

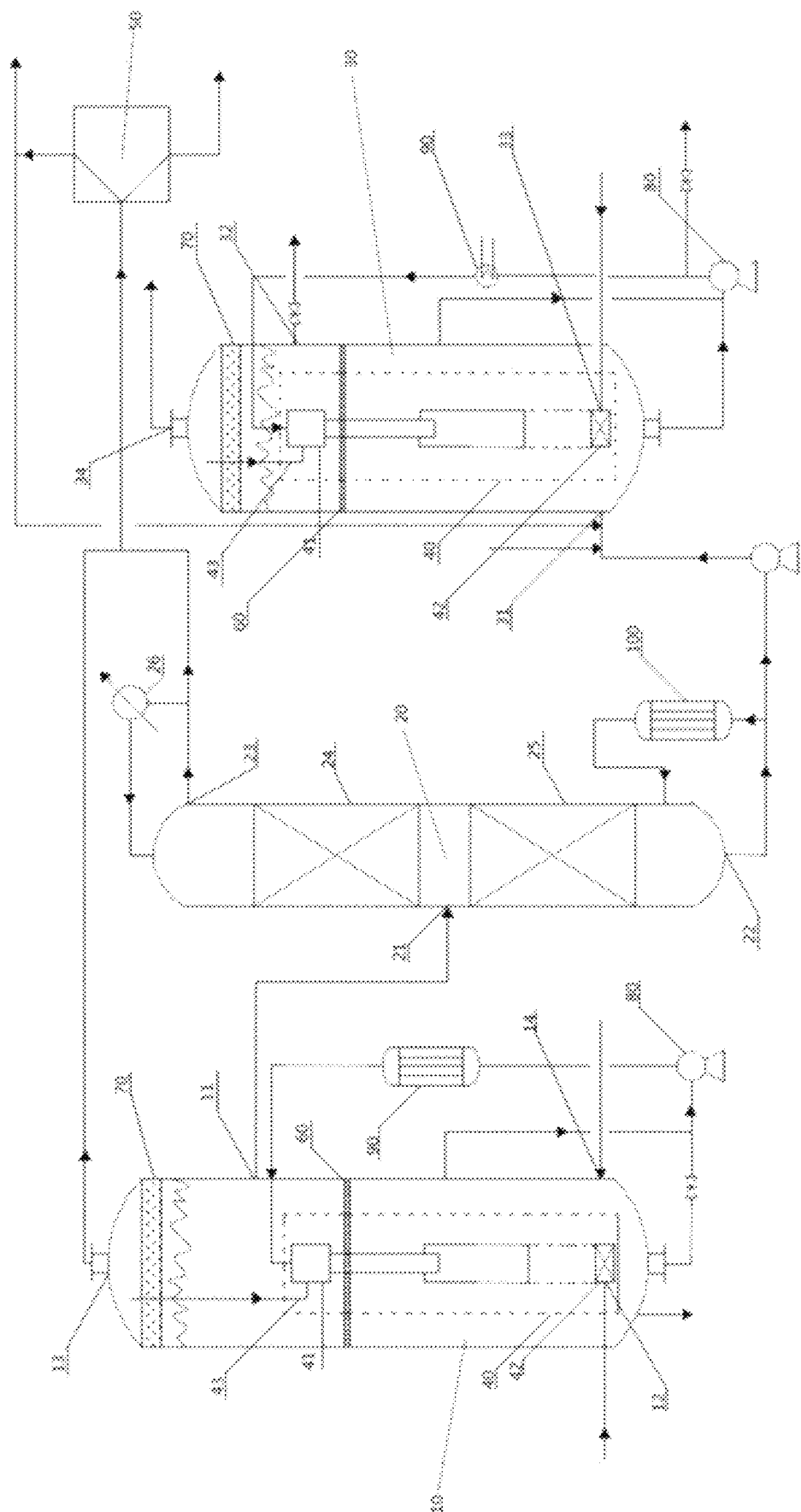

BUILT-IN MICRO-INTERFACE OXIDATION SYSTEM AND METHOD FOR PREPARING TEREPHTHALIC ACID FROM P-XYLENE

FIELD OF THE INVENTION

The present invention relates to the technical field of oxidation reaction for preparing terephthalic acid from p-xylene, in particular to a built-in micro-interface oxidation system and method for preparing terephthalic acid from p-xylene.

BACKGROUND OF THE INVENTION

Terephthalic acid is an important chemical raw material, which is usually prepared by oxidation reaction of p-xylene and oxygen-containing gas. A bubbling oxidation reactor is usually adopted as a reactor for p-xylene oxidation, and a diameter of bubbles is usually greater than 3 mm or even centimeter-sized. The area of a mass transfer boundary phase is limited, and the gas utilization rate is low, resulting in a low reaction efficiency. In order to strengthen gas-liquid mass transfer, a bubbling reactor is generally provided with tower plates, static mixers and other internal parts in the tower to enhance mixing. However, the diameter of the bubbles after mixing is usually 3-30 mm, and the area of the phase interface (liquid side and gas side) and the mass transfer coefficient are limited, so that the reaction performance is difficult to obtain a breakthrough improvement, and the whole efficiency of the reaction is further influenced. Therefore, a high-temperature and high-pressure operation is adopted in engineering, the mass transfer rate is improved by increasing the solubility of gas phase and/or liquid phase, thereby strengthening the reaction process. However, the process of p-xylene oxidation is very complicated and mainly includes 4 steps, namely p-xylene (PX)→p-Tolualdehyde (TALD)→p-toluic acid (p-TA)→p-carboxybenzaldehyde (4-CBA)→terephthalic acid (TA). The acetic acid is used as a solvent in the first two steps, high temperature and high pressure should not be used. The prior art adopts a mixed reaction process, which has high energy consumption, large consumption of acetic acid and low reaction efficiency.

In view of the above, the present invention is particularly proposed.

SUMMARY OF THE INVENTION

A first objective of the present invention is to provide a built-in micro-interface oxidation system for preparing terephthalic acid from p-xylene. A micro-interface unit is arranged in a reactor of the built-in micro-interface oxidation system, and air bubbles are broken into micro-level bubbles by the micro-interface unit, such that the phase interface area between a gas phase and a liquid phase is increased, the mass transfer space is fully satisfied, and the retention time of air in the liquid phase is increased. Therefore, the air consumption is reduced, the energy consumption is reduced, the operation temperature and the operation pressure are reduced, the reaction safety is improved, and a sectional process is adopted, so that a contradiction that an acetic acid solvent cannot withstand high-temperature oxidation conditions is solved, and the reaction efficiency is improved.

A second objective of the present invention is to provide a method for preparing terephthalic acid from p-xylene with the built-in micro-interface oxidation system, which is beneficial to reducing energy consumption and achieving better reaction effect than the prior art.

In order to achieve the above objectives of the present invention, the following technical schemes are adopted:

The present invention proposes a built-in micro-interface oxidation system for preparing terephthalic acid from p-xylene. The system includes a first reactor, a rectifying tower and a second reactor which are sequentially connected, wherein a first outlet is disposed on a side wall of the first reactor, a first inlet is disposed on a side wall of the second reactor, a material inlet is disposed on a side wall of the rectifying tower, and a material outlet is disposed at a bottom of the rectifying tower. The first outlet is connected with the material inlet of the rectifying tower, and the first inlet is connected with the material outlet of the rectifying tower. A plurality of micro-interface units are arranged in the first reactor and the second reactor and used for dispersing and crushing air into bubbles.

In the prior art, the reaction steps for preparing terephthalic acid from p-xylene are as follows:

Namely, p-xylene (PX)→p-Tolualdehyde (TALD)→p-toluic acid (p-TA)→p-carboxybenzaldehyde (4-CBA)→terephthalic acid (TA).

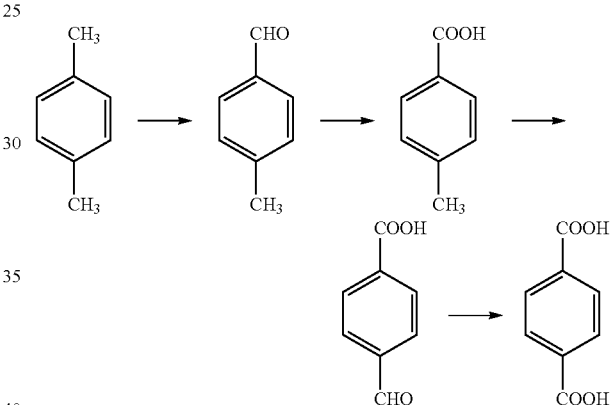

The reaction process generally adopts a bubbling oxidation reactor, the influence degree of phase interface area on volume mass transfer coefficient is larger in the generation process, and the general mass transfer efficiency of the bubbling oxidation reactor is lower, so that breakthrough progress on reaction efficiency is difficult, and the reaction efficiency and the raw material conversion rate are influenced. Through the micro-interface unit is arranged in the reactor of the built-in micro-interface oxidation system of the present invention, air and raw materials are introduced into the micro-interface unit, enhanced mass transfer and the dispersing and crushing are realized by the interior, micro-bubbles are formed by crushing, and the mass transfer space is fully satisfied, so that the air consumption is reduced. High reaction efficiency of the reaction can be ensured even if the temperature and the pressure are not required to be too high. In addition, the invention adopts a sectional process, which solves a contradiction that the acetic acid solvent cannot withstand the high-temperature oxidation condition, and improves the reaction efficiency.

Further, the micro-interface generators included in the micro-interface unit are not limited in the disposing manner, disposing position, or quantity. More preferably, the plurality of micro-interface units include a first micro-interface generator and a second micro-interface generator which are arranged up and down; the first micro-interface generator is connected with an air guide pipe, and a top end of the air guide pipe extends out of a liquid surface of the first reactor and is used for recovering air. A large amount of unreacted air and part of acetic acid and water vapor are accumulated above the reactor in the reaction process, and the unreacted air and part of acetic acid and water vapor enter the bottom of the reactor again through the gas guide pipe for multiple circulating reactions for full recovery, so that the mass transfer efficiency is improved. A second inlet is further disposed on the side wall of the first reactor, and a tail end of the second inlet extends into the second micro-interface generator; and a structure of the micro-interface unit in the second reactor is the same as that in the first reactor.

Preferably, the first micro-interface generator is a hydrodynamic micro-interface generator. Liquid phase materials (including p-tolualdehyde, acetic acid, water, a small amount of unreacted p-xylene, intermediate products and the like obtained by reaction) are used as power circulation, and a large amount of unreacted air above the reactor and part of acetic acid and water vapor are sucked in through the air guide pipe, so that the mass transfer effect between gas phase and liquid phase is increased, and the air on the liquid surface is fully recovered.

Further, a circulating pipeline for providing power for the first micro-interface generator is disposed on an outer side of the first reactor. Liquid-phase materials including p-tolualdehyde, acetic acid, water, a small amount of unreacted p-xylene, an intermediate product and the like obtained by reaction flow through the circulating pipeline. Specifically, one end of the circulating pipeline is communicated with the top of the first micro-interface generator, and the other end of the circulating pipeline is communicated with the side wall of the first reactor.

In addition, more preferably, the bottom of the first reactor is also provided with a pipeline, wherein materials in the pipeline mainly include p-tolualdehyde, acetic acid, water and the like. The pipeline is introduced from the top of the first micro-interface generator after being converged with the circulating pipeline to provide entrainment power for the first micro-interface generator to form circulating logistics, so that recycling of the materials is realized. The circulating pipeline is also provided with a circulating pump for providing power, the inner wall of the pump shell of the circulating pump is provided with a metal sensing probe, the outer wall of the pump shell on one side of the metal sensing probe is provided with a temperature sensor, and the metal sensing probe is connected with the temperature sensor through a lead wire, so that the temperature of the materials which are introduced into the circulating pump and are in a liquid phase can be monitored. A heat exchanger is further disposed on the circulating pipeline for controlling the temperature of the circulation materials to make the inside temperature of first reactor remain stable. Preferably, a plate heat exchanger is adopted. Compared with other heat exchangers, the plate heat exchanger has characteristics such as high heat exchange efficiency, small heat loss, energy saving, easy cleaning, and convenient removal.

Preferably, the second micro-interface generator is a pneumatic micro-interface generator.

The mass transfer effect is improved by introducing air into the micro-interface generator, contacting with reaction materials (including mixture of p-xylene, acetic acid, catalyst and the like) in the reactor, and then crushing to form micro-bubbles.

The first micro-interface generator is opposite to the outlet of the second micro-interface generator, so that bubbles generated by the first micro-interface generator move downwards, bubbles generated by the second micro-interface generator move upwards, and the bubbles collide with each other to generate smaller bubbles, thereby further increasing the contact area, and accelerating the reaction efficiency.

Furthermore, a connecting rod for fixing the first micro-interface generator and the second micro-interface generator is disposed between the first micro-interface generator and the second micro-interface generator. The connecting rod plays a good role in reinforcing so as to prevent the flow of liquid in the reactor from impacting the first micro-interface generator and the second micro-interface generator. The concrete material, shape and quantity of the connecting rod are not restricted, as long as can play a fixed effect, preferably a long rod shape.

It can be understood by those skilled in the art that the micro-interface generator used in the present invention is embodied in the prior patent of the present inventor, such as the patent with a publication No. 106215730A. The core of the micro-interface generator is bubble breaking, and the principle of the bubble breaking is that the gas carried by the high-speed jet flow collides with each other to perform energy transfer, so as to break the bubbles. The structure of the micro-interface generator, is disclosed in one embodiment of the above-mentioned patent, and details are omitted. The connection between the micro-interface generator and the first and second reactors and other devices, including the connection structure and the connection position, depends on the structure of the micro-interface generator, which is not limited. The reaction mechanism and the control method of the micro-interface generator have been disclosed in the inventor's prior patent CN107563051B, and are not described in detail herein.

The internal structure of the second reactor is in conformity with that of the first reactor. The difference between them is that the material inlet and the material outlet of the first reactor are different from those of the second reactor.

The mixed raw material inlet of the first reactor is disposed on a lower position of the side wall, and the air enters the second inlet, and the mixed raw materials of reaction (including a mixture such as p-xylene, acetic acid and catalyst) enter the mixed raw material inlet. The first outlet of the first reactor is disposed on a middle-upper portion of the side wall, and an intermediate product (the principal ingredients is methylbenzoic acid, and further includes acetic acid, water, a small amount of unreacted p-xylene, intermediate product etc.) is generated through an overflow pipe, and gets into the middle part of rectifying tower, for performing a purification separation in the rectifying tower.

The position of the first inlet of the second reactor is the same as the position of the second inlet of the first reactor. The materials (p-methylbenzoic acid and water) produced at the bottom of the rectifying tower, the supplemented catalyst (hydrobromic acid) and the water separated from the acid-water separator, enter the second reactor from the first inlet to continue to react. The air enters from the air inlet of the second reactor, such that the generated terephthalic acid solution after full reaction is extracted from the third outlet at the upper part of the side wall of the second reactor.

Furthermore, the first micro-interface generator is fixed inside the first reactor and the second reactor by a wave-proof grid, wherein the wave-proof grid mainly plays a role of isolation support and foam filtering. On one hand, the first micro-interface reactor is fixed inside the reactor, on the other hand, entrained mist is removed, so that the mass transfer efficiency is ensured, and the loss of valuable materials is reduced. The wave-proof grid can be made of domestic imported high-quality materials, such as: Q235, 304, 304L, 321, 316L, F46, NS-80, nickel wire, titanium wire and alloy.

Further, both interior tops of the first reactor and the second reactor are provided with filter screens. A large amount of unreacted air and some gaseous substances are accumulated at the top of the reactors, and these gases enter the first micro-interface generator through the air guide pipe. The filter screens can prevent impurities in the gas from getting into the first micro-interface generator.

Further, a second outlet is further disposed at the top of the first reactor, and the second outlet is connected with an acid-water separator. Part of acetic acid and water extracted from the top of the rectifying tower and tail gas extracted from the top of the first reactor are jointly converged and then enter the acid-water separator. The separated acetic acid returns to the first reactor again for recycling, part of the separated water is discharged, and part of the separated water enters the second reactor for recycling.

Further, the rectifying tower adopted by the invention mainly includes a light-component separation section and a heavy-component separation section. A material inlet is disposed on a tower section between the light-component separation section and the heavy-component separation section, and is used for introducing an oxidation product in the first reactor into the rectifying tower. The materials coming in from the material inlet of the rectifying tower mainly include p-toluic acid, and also include acetic acid, water, a small amount of unreacted p-xylene, an intermediate product, etc. The p-toluic acid and the small amount of water are rectified and separated to the bottom of the rectifying tower through the heavy-component separation section located below the material inlet. The acetic acid and most water are rectified and separated towards the top of the rectifying tower after passing through the light-component separation section. The acetic acid and the water vapor led out from a distillate outlet are condensed, a part of the water is returned to the rectifying tower from the top of the tower as a reflux liquid, and the rest of the water is mixed with a tail gas in the first reactor through a pipeline and then enters an acid-water separator. After liquid phase materials such as p-toluic acid and a small amount of water which are extracted from the tower bottom products, one part of the liquid phase materials passes through a tower kettle reboiler and then returns to the heavy-component separation section as the reflux liquid to be continuously rectified, and the other part of the liquid phase materials is introduced into the first inlet to enter the second reactor to be continuously reacted.

The light-component separation section and the heavy-component separation section in the rectifying tower can be formed by any combination of a plurality of tower plates and packings. Preferably, the tower plate structure is adopted at the position close to the tower kettle, and the packing structure is adopted at the position close to the top of the tower, because the pressure drop of the tower plates is relatively large, and the pressure drop of the packings relatively small.

Further, the top of the rectifying tower is provided with a tower top condenser, the tower kettle is provided with a tower kettle reboiler. The type of the tower kettle reboiler is a falling film reboiler. Compared with the common reboiler type, the falling film reboiler forms a film on the pipe wall, which has high heat exchange efficiency and short residence time, and is not easy to coke, thereby avoiding the formation of byproducts due to polymerization of substances in the tower kettle.

In addition, the invention also provides a method for preparing terephthalic acid from p-xylene with the built-in micro-interface oxidation system, which includes the following steps:
  dispersing and crushing air through the micro-interface unit arranged in the first reactor;
  a reaction material entering the first reactor to react with the dispersed and crushed air;
  a liquid phase material obtained by the reaction entering the rectifying tower for separation; and
  the material separated by the rectifying tower entering the second reactor to react with the dispersed and crushed air to obtain the terephthalic acid.

Preferably, a temperature in the first reactor is 120-155° C. and a pressure in the first reactor is 0.20-0.66 MPa.

Preferably, a temperature in the second reactor is 135-180° C. and a pressure in the second reactor is 0.56-0.82 MPa.

Compared with the prior art, the invention has the following beneficial effects:
  (1) By arranging the micro-interface unit in the system of the present invention, the contact area is increased, the mass transfer efficiency between reaction phases is improved, such that the objective of strengthening the reaction in a lower pressure range is further achieved, the reaction efficiency is improved, the energy consumption and the generation cost in the reaction process are greatly reduced, the investment intensity is reduced, the equipment operation period is prolonged, the intrinsic safety in the reaction process is ensured, and the industrial large-scale production of reaction finished products is effectively ensured.
  (2) The invention provides different reaction conditions aiming at different reactions through a sectional process, solves the contradiction that acetic acid cannot withstand high-temperature oxidation conditions as a solvent in the process of preparing terephthalic acid from p-xylene. The product can be taken out in time, and the sectional oxidation is favorable for reducing investment and consumption, and achieves better reaction effect than the existing process.

BRIEF DESCRIPTION OF THE DRAWINGS

Upon reading the following detailed description of preferred embodiments, various advantages and benefits will be apparent to those of ordinary skill in the art. The drawings are for the purpose of explaining preferred embodiments only, and do not constitute improper limitations on the present invention. The same components are also denoted by the same reference numerals throughout the drawings. In the drawings:

The drawing is a structural diagram of a built-in micro-interface strengthening oxidation system for preparing terephthalic acid from p-xylene according to an embodiment of the present invention.

DESCRIPTION OF THE PREFERRED EMBODIMENTS

The technical schemes of the present invention will be clearly and completely described below with reference to the accompanying drawings and specific embodiments, but those skilled in the art will understand that the embodiments described below are part of the embodiments of the present invention, rather than all of the embodiments. It is only used to illustrate the present invention and should not be construed as limiting the scope of the present invention. Based on the embodiments of the present invention, all other embodiments obtained by those of ordinary skill in the art without creative efforts shall fall within the protection scope of the present invention. If the specific conditions are not indicated in the examples, it is carried out according to the conventional conditions or the conditions suggested by the manufacturer. The reagents or instruments used without the manufacturer's indication are conventional products that can be purchased from the market.

In the description of the present invention, it should be noted that the terms "center", "upper", "lower", "left", "right", "vertical", "horizontal", "inner", "outer", etc., indicate orientations or positional relationships based on the orientations or positional relationships shown in the drawings, and are only for convenience of description and simplicity of description, but do not indicate or imply that the device or element being referred to must have a particular orientation, be constructed and operated in a particular orientation, and thus, should not be construed as limiting the present invention. Furthermore, the terms "first," "second," and "third" are used for descriptive purposes only and are not to be construed as indicating or implying relative importance.

In the description of the present invention, it should be noted that, unless otherwise explicitly specified or limited, the terms "mounted," "connected," and "coupled" are to be understood broadly, e.g., as meaning either a fixed connection, a removable connection, or an integral connection; can be mechanically or electrically connected; they may be connected directly or indirectly through intervening media, or they may be interconnected between two elements. The specific meanings of the above terms in the present invention can be understood in specific cases to those skilled in the art.

In order to more clearly illustrate the technical schemes of the present invention, the following descriptions are given in the form of specific embodiments.

EMBODIMENTS

Referring to the drawing. A built-in micro-interface oxidation system for preparing terephthalic acid from p-xylene includes a first reactor 10, a rectifying tower 20 and a second reactor 30.

A first outlet 11 is disposed on a side wall of the first reactor 10, a second inlet 12 and a mixed raw material inlet 14 are disposed at a lower part of the opposite side wall, and a second outlet 13 is disposed at the top of the first reactor 10. The materials coming out from the second outlet 13 are mainly acetic acid and water vapor.

A material inlet 21 is disposed on the side wall of the rectifying tower 20, a material outlet 22 is disposed at the bottom of the rectifying tower 20, a first inlet 31 is disposed at a lower position of the side wall of the second reactor 30, and an air inlet 33 extends into the second micro-interface generator 42 in the second reactor 30. The first outlet 11 is connected with the material inlet 21, the first inlet 31 is connected with the material outlet 22, the mixed raw material and air carry out a primary oxidation reaction in the first reactor 10, the products obtained after the oxidation reaction (main components are p-toluic acid, acetic acid, water, a small amount of unreacted p-xylene, intermediate products and the like) enter the rectifying tower 20 through the first outlet 11 for separation. The products (p-toluic acid, water and the like) separated at the bottom of the tower enter the second reactor 30 from the first inlet 31 through the material outlet 22 for secondary oxidation reaction. The reaction products obtained after the secondary oxidation reaction are collected from a third outlet 32 on the side wall of the second reactor 30.

A plurality of micro-interface units 40 are arranged in the first reactor 10 and the second reactor 30 for dispersing and crushing air or the mixture into bubbles. The plurality of micro-interface units 40 include a first micro-interface generator 41 and a second micro-interface generator 42 arranged up and down. The first micro-interface generator 41 is connected with an air guide pipe 43, and a top end of the air guide pipe 43 extends out of a liquid surface of the first reactor 41. The first micro-interface generator 41 is a hydraulic micro-interface generator, so as to realize the entrainment of the unreacted air and part of the gas material above the reactor. The power of the first micro-interface generator 41 is given by circulating materials (including p-tolualdehyde, acetic acid, water, a small amount of unreacted p-xylene, intermediate products, etc.) provided by a circulating pump 80. The above-mentioned circulating materials enter the first micro-interface generator 41 after the heat exchange of the heat exchanger 90 to provide power to entrain the gas. The end of the second inlet 12 extends into the second micro-interface generator 42. The air contacts the reaction material in the micro-interface generator after entering from the second inlet 12, which increases the contact area between the gas phase and liquid phase, and improves the mass transfer effect.

Furthermore, the tail gas of the first reactor 10 is discharged through the second outlet 13 at the top, and the product enters the rectifying tower 20 through the first outlet 11 for separation. The rectifying tower 20 mainly has a light-component separation section 24 and a heavy-component separation section 25. Part of the separated light-component acetic acid and water is returned to the rectifying tower 20 through a condenser 26 from the top of the tower as a reflux liquid, and another part of the acetic acid and water enters an acid-water separator 50 through a distillate outlet 23 after mixing with the tail gas discharged from the second outlet 13. The separated water enters the second reactor 30, and the acetic acid is returned to the first reactor 10 for recycling. Part of the heavy-component product (p-tolutic acid and water, etc.) of the material outlet 22 at the bottom of the rectifying tower 20 passes through the tower kettle reboiler 100 as a reflux liquid and returns to the heavy-component separation section 25 to continue rectification, and the other part enters the second reactor 30 through the first inlet 31 for secondary oxidation reaction.

The end of the air inlet 33 extends into the second micro-interface generator 42 in the second reactor 30. The structure of the micro-interface generator disposed in the second reactor 30 is the same as that in the first reactor 10. The reaction product, the terephthalic acid, is extracted from a third outlet 32 located at the upper side wall of the second reactor 30. The top of the second reactor 30 is also provided with an exhaust gas outlet 34. The exhaust gas enters the subsequent treatment stage from the exhaust gas outlet 34, and is discharged to the atmosphere after reaching the standard.

In the above embodiments, the temperature in the first reactor 10 is 120-155° C., and the pressure in the first reactor 10 is 0.20-0.66 MPa; the temperature in the second reactor 30 is 135-180° C., and the pressure in the second reactor 30 is 0.56-0.82 MPa.

In the above embodiments, there is not specific requirement for the number of the pump bodies, which can be set at corresponding positions as required. In addition, the tower height, the tower diameter, the number of tower plates and the tower division manner of the rectifying tower 20 can be adjusted based on actual needs.

In the above embodiments, the number of the micro-interface generators is not limited. In order to increase the dispersion and mass transfer effect, additional micro-interface generators can also be added. In particular, the installation positions of the micro-interface generators are not limited. The micro-interface generators can be installed externally or built-in, and they can also be installed in a way of being opposite to each other on the side walls of the tower kettle, so as to realize the hedging of the micro-bubbles coming out of the outlet of the micro-interface generators.

In the above embodiments, the first micro-interface generator 41 and the second micro-interface generator 42 are both fixed inside the reactor by using wave-proof grids 60.

In the above embodiments, filter screens 70 are provided above the liquid surface of the first reactor 10 and the second reactor 30 to separate out air and some gaseous substances.

The working process and principle of the built-in micro-interface oxidation system for preparing terephthalic acid from p-xylene of the present invention are briefly described below.

The mixture of p-xylene, acetic acid and catalyst (cobalt acetate, manganese acetate) enters the first reactor 10 from the mixed raw material inlet 14, and air enters the second micro-interface generator 42 from the second inlet 12 for dispersion and crushing. The mixed raw materials and the crushed air undergo an oxidation reaction in the first reactor 10. During the reaction, the material and liquid inside the first reactor 10 provide power circulation to the first micro-interface generator 41 through the circulating pipeline. A large amount of unreacted air and part of water vapor above the reactor are drawn back to the bottom of the reactor through the first micro-interface generator 41 to continue to participate in the reaction.

The product obtained after fully reacting (the main component is p-toluic acid, also includes acetic acid, water, a small amount of unreacted p-xylene, intermediate products, etc.) enters the rectifying tower 20 through the first outlet 11. The acetic acid and water are separated by rectification towards the top of the tower after passing through the light-component separation section 24, wherein a part of acetic acid and water vapor drawn from the distillate outlet 23 of the rectifying tower 20 is recirculated into the rectifying tower 20 through the condenser 26, and another part of the acetic acid and water is mixed with the tail gas discharged from the second outlet 13 through the pipeline and then enters the acid-water separator 50. The water separated by the acid-water separator 50 enters the second reactor 30, the acetic acid is returned to the first reactor 10 for recycling. A part of the heavy-component products (p-toluic acid and water, etc.) produced by the material outlet 22 at the bottom of the rectifying tower 20 is returned to the rectifying tower after the reboiler treatment of the tower kettle reboiler 100, and the other part enters the second reactor 30 through the first inlet 31. The air inlet 33 on the other side wall of the second reactor 30 is fed with air. After being crushed by the second micro-interface reactor 42, the crushed air undergoes an oxidation reaction with the heavy-component products (p-toluic acid and water, etc.). The structure of the micro-interface generator arranged in the second reactor 30 is the same as that in the first reactor 10. The product, terephthalic acid solution is produced through the third outlet 32 and enters the post-processing refining and separation section. After the exhaust gas is extracted from the exhaust gas outlet 34 of the second reactor 30, the subsequent treatment stage is performed. After reaching the standard, it is discharged to the atmosphere.

The above process steps are cycled back and forth to make the entire processing system run smoothly.

Finally, it should be noted that the above embodiments are only used to illustrate the technical schemes of the present invention, but not to limit them. Although the present invention has been described in detail with reference to the foregoing embodiments, those of ordinary skill in the art should understand that: the technical schemes described in the foregoing embodiments can still be modified, or some or all of the technical features thereof can be equivalently replaced. However, these modifications or substitutions do not make the essence of the corresponding technical schemes depart from the scope of the technical schemes of the embodiments of the present invention.

What is claimed is:

1. A built-in micro-interface oxidation system for preparing terephthalic acid from p-xylene, comprising:
    a first reactor, a rectifying tower and a second reactor which are sequentially connected, wherein a first outlet is disposed on a side wall of the first reactor, a first inlet is disposed on a side wall of the second reactor, a material inlet is disposed on a side wall of the rectifying tower, and a material outlet is disposed at a bottom of the rectifying tower;
    the first outlet is connected with the material inlet of the rectifying tower, and the first inlet is connected with the material outlet of the rectifying tower;
    a plurality of micro-interface units are arranged in the first reactor and the second reactor and used for dispersing and crushing air into bubbles;
    wherein the plurality of micro-interface units comprise a first micro-interface generator and a second micro-interface generator which are arranged up and down; the first micro-interface generator is connected with an air guide pipe, and a top end of the air guide pipe extends out of a liquid surface of the first reactor and is used for recovering air; a second inlet is further disposed on the side wall of the first reactor, and a tail end of the second inlet extends into the second micro-interface generator; and a structure of the micro-interface unit in the second reactor is the same as that in the first reactor;
    wherein the first micro-interface generator is fixed inside the first reactor and the second reactor by using wave-proof grids;
    wherein both interior tops of the first reactor and the second reactor are provided with filter screens.

2. The built-in micro-interface oxidation system according to claim 1, wherein the first micro-interface generator is a hydrodynamic micro-interface generator.

3. The built-in micro-interface oxidation system according to claim 1, wherein the second micro-interface generator is a pneumatic micro-interface generator.

4. The built-in micro-interface oxidation system according to claim 1, wherein a second outlet is further disposed at a top of the first reactor, and the second outlet is connected to an acid-water separator.

5. A method for preparing terephthalic acid from p-xylene with a built-in micro-interface oxidation system according to claim 1, comprising the steps of:
    dispersing and crushing air through the micro-interface unit arranged in the first reactor;
    a reaction material entering the first reactor to react with the dispersed and crushed air;

a liquid phase material obtained by the reaction entering the rectifying tower for separation; and the material separated by the rectifying tower entering the second reactor to react with the dispersed and crushed air to obtain the terephthalic acid.

6. The method according to claim 5, wherein a temperature in the first reactor is 120-155° C. and a pressure in the first reactor is 0.20-0.66 MPa.

7. The method according to claim 5, wherein a temperature in the second reactor is 135-180° C. and a pressure in the second reactor is 0.56-0.82 MPa.

* * * * *